US010620224B2

(12) United States Patent
Wetzel et al.

(10) Patent No.: US 10,620,224 B2
(45) Date of Patent: *Apr. 14, 2020

(54) FISH SEXUAL CHARACTERISTIC DETERMINATION USING PEPTIDE HORMONES

(71) Applicant: Mote Marine Laboratory, Inc., Sarasota, FL (US)

(72) Inventors: Dana L. Wetzel, Sarasota, FL (US); John E. Reynolds, Sarasota, FL (US); William E. Roudebush, Charleston, SC (US)

(73) Assignee: Mote Marine Laboratory, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,159

(22) Filed: May 12, 2017

(65) Prior Publication Data

US 2017/0248619 A1 Aug. 31, 2017

Related U.S. Application Data

(62) Division of application No. 13/990,022, filed as application No. PCT/US2011/062032 on Nov. 23, 2011, now Pat. No. 9,651,565.

(60) Provisional application No. 61/417,803, filed on Nov. 29, 2010.

(51) Int. Cl.
*G01N 33/53* (2006.01)
*A61K 38/18* (2006.01)
*A61K 38/00* (2006.01)
*G01N 33/74* (2006.01)

(52) U.S. Cl.
CPC ....... *G01N 33/74* (2013.01); *G01N 2333/495* (2013.01)

(58) Field of Classification Search
None
See application file for complete search history.

(56) References Cited

U.S. PATENT DOCUMENTS

| 3,859,522 A | 1/1975 | Cuthbert |
| 5,013,906 A | 5/1991 | Miyakawa et al. |
| 5,364,837 A | 11/1994 | Burger et al. |
| 5,480,774 A | 1/1996 | Hew et al. |
| 7,241,577 B2 | 7/2007 | Seifer et al. |
| 2006/0046274 A1 | 3/2006 | Segal et al. |
| 2006/0166277 A1 | 7/2006 | Karumanchi et al. |
| 2009/0317921 A1 | 12/2009 | Groome et al. |

FOREIGN PATENT DOCUMENTS

CA 2072231 A1 12/1993

OTHER PUBLICATIONS

Bilezikjian et al. 2006. Reproduction 132:207-215 (Year: 2006).*
International Search Report and Written Opinion for corresponding International Application No. PCT/US2011/062032 dated Jul. 18, 2012; 10 pages.
Vecsei et al., "A noninvasive technique for determining sex of live adult North American sturgeons", Environmental Biology of Fishes 68: 333-338 (2003).
Rainer, "Genetic sex determination in sturgeons: practical application in caviar production", IST World, 2 pages (2003).
Henderson-Arzapalo et al., "Determination of sex by molecular genetic methods in Atlantic sturgeon", USGS Study Plan No. 02085, 4 pages (2004).
Colombo et al., "Use of Ultrasound Imaging to Determine Sex of Shovelnose Sturgeon", North American Journal of Fisheries Management 24:322-326 (2004).
Craig, "Successful stepping stones to sex identification of lake sturgeon by blood plasma hormones", Preliminary Proceedings of the 2008 Great Lakes Lake Sturgeon Coordination Meeting (2008).
Craig et al., "Sex assignment of lake sturgeon (Acipenser fluvescens) based on plasma sex hormone and vitellogenin levels", Journal of Applied Ichthyology Special Issue: Proceedings of the Inaugural Meeting of the North American Chapter of the World Sturgeon Conservation Society, Ottawa, Canada, Aug. 19-21, 2008, 25, Issue Supplement s2, pp. 60-67 (Oct. 2009).
Keyvanshokooh et al., "A review of sex determination and searches for sex-specific markers in sturgeon", Aquaculture Research, 41, Issue 9, pp. e1-e7 (Aug. 2010).
Pala, I. et al., "Expression pattern of anti-Müllerian hormone (amh) in the hybrid fish complex of Squalius alburnoides", Science Direct, Gene, 410, pp. 249-258 (2008).
Lankford, Scott E. et al., "The maturation-inducing hormone 17α20ß-dihydroxy-4-pregnen-3-one regulates gene expression of inhibin ß$_A$ and bambi (bone morphogenetic protein and activin-membrane-bound inhibitor) in the rainbow trout ovary", General and Comparative Endocrinology, 168, pp. 369-376 (2010).
Ijiri, S. et al., "Sexual Dimorphic Expression of Genes in Gonads During Early Differentiation of a Teleost Fish, the Nile Tilapia Oreaochromis niloticus", Biology of Reproduction, 78, pp. 333-341 (2008).
"Kazakh fish farmer helps spawn country's sturgeon farming industry", Universal Newswires, Sep. 15, 2010, downloaded from the Internet at: http://www.universalnewswires.com/centralasia/viewstory.aspx?id=1698.
Vizziano, D. et al., "Characterization of Early Molecular Sex Differentiation in Rainbow Trout, Oncorhynchus mykiss", Developmental Dynamics, 236, pp. 2198-2206 (2007).
Re, Richard N., "The intracrine hypothesis and intracellular peptide hormone action", Wiley Periodicals, Inc., BioEssays, vol. 25, pp. 401-409 (2003).

(Continued)

Primary Examiner — Shulamith H Shafer
(74) Attorney, Agent, or Firm — Patterson Thuente Pedersen, P.A.

(57) ABSTRACT

Fish sexual characteristics are determined by measuring the concentration in fish serum, plasma or whole blood of one or more peptide hormones of the transforming growth factor-beta superfamily (TGF-β superfamily). The disclosed method and an accompanying field test kit may be used in sturgeon aquaculture to cull out young male fish so that increased time and resources may be devoted to the further rearing of female fish for caviar production. The method and test kit may also be used for wild fish life history studies.

20 Claims, 5 Drawing Sheets

(56) References Cited

OTHER PUBLICATIONS

Knight, Phil G., et al., "TGF-β superfamily members and ovarian follicle development", Reproduction Review, vol. 132, pp. 191-206 (2006).

BioAssay Works®, Products, overview information, 2 sheets, web capture for Feb. 1, 2010 downloaded from the Internet Archives at: https://web.archive.org/web/20100201162221/http://www.bioassayworks.com/products.html.

Chembio Diagnostic Systems, Inc., Rapid Tests for Earlier Treatment, product information, 3 sheets, web capture for Aug. 14, 2010 downloaded from the Internet Archives at: https://web.archive.org/web/20100814161530/http://www.chembio.com.

Clark et al., Transforming growth factor-beta (TGF-62 ), The International Journal of Biochemistry & Cell Biology, 30, pp. 293-298 (1998).

Bilezikjian et al., Pituitary actions of ligands of the TGF-62 family: activins and inhibins, Society for Reproduction and Fertility, 132, pp. 207-215 (2006).

Volff et al., Medaka dmY/dmrt1Y is not the universal primary sex-determining gene in fish, Trends in Genetics, vol. 19, pp. 196-199 (Apr. 2003).

Kalra et al., Development of a second generation Inhibin B ELISA, Journal of Immunological Methods, 362, pp. 22-31, epub 21 (Aug. 4010).

Pigny et al., Serom Anti-Müllerian Hormone as a Surrogate for Antral Follicle Count for Definition of the Polycystic Ovary Syndrome, The Journal of Clinical Endocrinology & Metabolism 91 (3): pp. 941-945 (2006).

McCormick et al., Multiple molecular approaches yield no evidence for sex-determining genes in lake sturgeon, J. Appl. Icthyol. 24, pp. 643-645 (2008).

2012. How do I Tell the Sex of My Fish? http://www.allaquariuminfo.com/2012/01/how-do-i-tell-sex-of-my-fish.html downloaded Jun. 3, 2015.

U.S. Appl. No. 13/990,022, now allowed and scheduled to issue as now U.S. Pat. No. 9,651,565.

Partial European Search Report dated Mar. 8, 2018; 12 pages.

* cited by examiner

FISH SEXUAL CHARACTERISTIC DETERMINATION USING PEPTIDE HORMONES

CROSS REFERENCE TO RELATED APPLICATION

This application is a division of U.S. patent application Ser. No. 13/990,022 filed May 28, 2013, now allowed, which is a national stage filing under 35 U.S.C. § 371 of International Application No. PCT/US2011/062032 filed Nov. 23, 2011 and which claims priority under 35 U.S.C. § 119 to U.S. Provisional Application No. 61/417,803 filed Nov. 29, 2010, the disclosures of each of which are incorporated herein by reference.

TECHNICAL FIELD

The present invention relates to fisheries research and aquaculture.

BACKGROUND

For certain commercially important fish such as sturgeon (family Acipenseridae), adult female fish have enormous value for their roe or caviar. The meat from male fish has only limited economic value, and the cost of rearing males to maturity can far exceed the value of their meat.

The various sturgeon species reach sexual maturity at somewhat different ages, and within each species may reach sexual maturity at differing ages based on factors including food availability and nutritional status. Farm-reared fish may be better fed and faster growing than their wild counterparts, and may reach sexual maturity earlier than in the wild. Scientists at Mote Marine Laboratory's Aquaculture Park (MAP), an indoor aquaculture facility, have found that farm-reared male and female Siberian sturgeon reach sexual maturity at around five years of age, at which point roe can be harvested from female fish. Harvesting involves cutting open the fish, at which point visual inspection can distinguish gender. This gender-determination technique is however lethal to the fish and involves rearing them until they reach maturity.

In aquaculture enterprises, it would be extremely useful to determine the gender of very young (for example, age three or younger) male and female sturgeon in a nonlethal manner. Doing so would allow sturgeon farmers to remove young males and thereby avoid the costs associated with several additional years of rearing less valuable male fish, focus resources on the care and raising of highly valuable female fish, and optimize use of available tank space. Nonlethal methods for early fish gender determination include those described in Vecsei et al., "A noninvasive technique for determining sex of live adult North American sturgeons", *Environmental Biology of Fishes* 68: 333-338 (2003); Rainer, "Genetic sex determination in sturgeons: practical application in caviar production", IST World (2003); Henderson-Arzapalo et al., "Determination of sex by molecular genetic methods in Atlantic sturgeon", USGS Study Plan Number 02085 (2004); Colombo et al, "Use of Ultrasound Imaging to Determine Sex of Shovelnose Sturgeon", *North American Journal of Fisheries Management* 24: 322-326 (2004), Craig, "Successful stepping stones to sex identification of lake sturgeon by blood plasma hormones", Preliminary Proceedings of the 2008 Great Lakes Lake Sturgeon Coordination Meeting (2008); Craig et al., "Sex assignment of lake sturgeon (*Acipenser fluvescens*) based on plasma sex hormone and vitellogenin levels", Journal of Applied Ichthyology Special Issue: Proceedings of the Inaugural Meeting of the North American Chapter of the World Sturgeon Conservation Society, Ottawa, Canada, Aug. 19-21, 2008, 25, Issue Supplement s2, pp. 60-67 (October, 2009); and Keyvanshokooh et al., "A review of sex determination and searches for sex-specific markers in sturgeon", Aquaculture Research, 41, Issue 9, pp. e1-e7 (August 2010). However, existing gender determination methods generally lack sufficient accuracy or ease of use, especially in young fish.

SUMMARY OF THE INVENTION

The present invention describes, in one aspect, a method for fish sexual characteristic determination, which method comprises collecting blood from fish; optionally separating serum or plasma from such blood; measuring the concentration in such serum, plasma or blood of one or more peptide hormones of the transforming growth factor-beta superfamily (TGF-β superfamily); and determining a desired fish sexual characteristic based on such peptide hormone concentration. Exemplary fish sexual characteristics which may be determined using the disclosed method include fish gender, readiness for breeding, readiness for roe harvesting and assessment of environmental or other factors influencing sexual development, sexual selection or hermaphroditism. The disclosed method may for example be used to determine gender and distinguish between male and female fish with high accuracy at very early ages, for example at as little as 12 months and possibly even younger for Siberian sturgeon. The disclosed method has been used to correctly identify gender in fish for which ultrasound analysis yielded inaccurate gender determination.

The invention provides, in another aspect, a field test kit for fish sexual characteristic determination, comprising a hand-held device having a plurality of test sites that can accept a blood, serum or plasma sample from a fish and indicate a peptide hormone concentration, each test site comprising a support bearing a rapid-acting capture antibody and a rapid-developing reporter antibody or other indicator that provides a colorimetric or other indication of such peptide hormone concentration in less than 15 minutes after exposure of the support to such sample.

The invention provides, in yet another aspect, a field test kit for fish sexual characteristic determination, comprising a support bearing a rapid-acting capture antibody and a rapid-developing reporter antibody or other indicator that provides a colorimetric or other indication of peptide hormone concentration in less than three minutes after exposure of the support to a blood, serum or plasma sample from a fish, and with 90% or greater accuracy when compared to histologically determined data.

DETAILED DESCRIPTION

Figure 1:
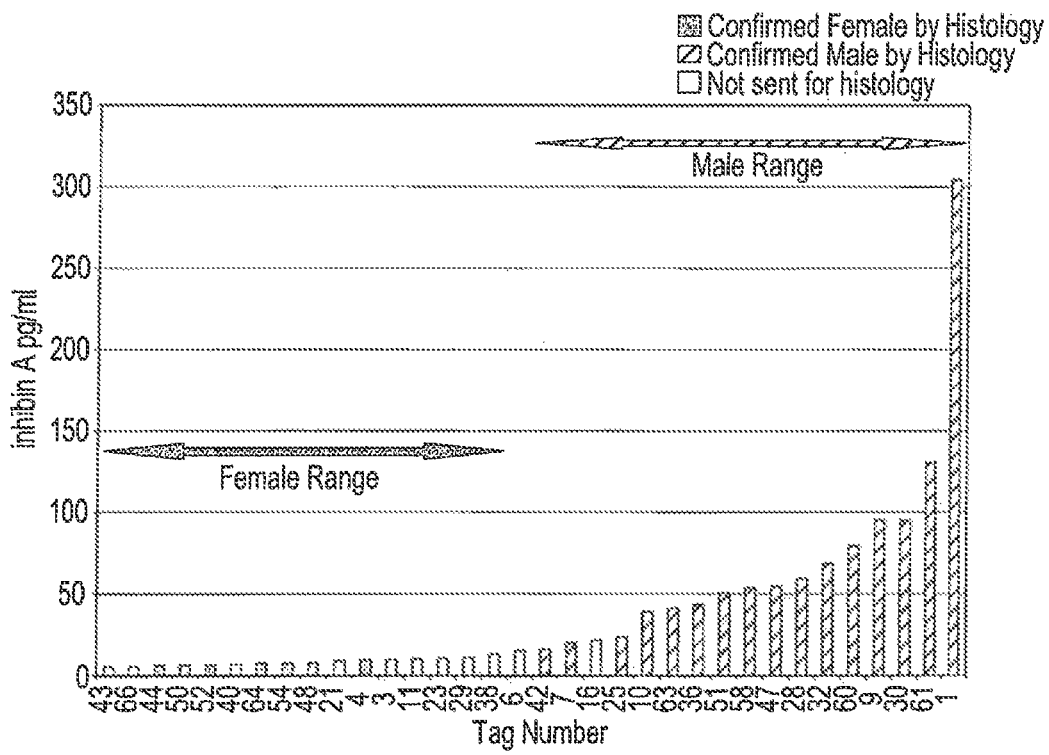
FIG. 1, FIG. 2 and FIG. 3 are graphs illustrating Inhibin A concentrations in collections of 16 month, 32 month and 39 month old Siberian sturgeon.

The disclosed method and field test kit may be used to determine fish sexual characteristics in a variety of so-called "bony fishes" (class Osteichthyes) of two subclasses, the Chondrostei and the Teleostei, including species that can be reared in aquaculture systems. The fish from the subclass Chondrostei (which have primarily cartilaginous skeletons, with some ossification) may for example be from the family Acipenseridae, including fish species of the genus *Acipenser* such as Adriatic sturgeon (*Acipenser naccarii*), Amur sturgeon (*Acipenser schrenckii*), Atlantic sturgeon (*Acipenser oxyrinchus oxyrinchus*), Baikal sturgeon (*Acipenser baerii baicalensis*), Baltic or European sturgeon (*Acipenser sturio*), Chinese sturgeon (*Acipenser sinensis*), fringebarbel sturgeon (*Acipenser nudiventris*), green sturgeon (*Acipenser medirostris*), Gulf sturgeon (*Acipenser oxyrinchus desotoi*), Japanese sturgeon (*Acipenser multiscutatus*), lake sturgeon (*Acipenser fulvescens*), Persian sturgeon (*Acipenser persicus*), Russian sturgeon (*Acipenser gueldenstaedtii*), Sakhalin sturgeon (*Acipenser mikadoi*), shortness sturgeon (*Acipenser brevirostrum*), Siberian sturgeon (*Acipenser baerii baerii*), starry sturgeon (*Acipenser stellatus*), sterlet (*Acipenser ruthenus*), white sturgeon (*Acipenser transmontanus*) and Yangtze sturgeon (*Acipenser dabryanus*); fish species of the genus *Huso* such as beluga sturgeon (*Huso huso*) and Kaluga sturgeon (*Huso dauricus*); fish species of the genus *Scaphirhynchus* such as Alabama sturgeon (*Scaphirhynchus suttkusi*), pallid sturgeon (*Scaphirhynchus albus*) and shovelnose sturgeon (*Scaphirhynchus platorynchus*); and fish species of the genus *Pseudoscaphirhynchus* such as Amu Darya sturgeon (*Pseudoscaphirhynchus kaufmanni*), dwarf sturgeon (*Pseudoscaphirhynchus hermanni*) and Syr Darya sturgeon (*Pseudoscaphirhynchus fedtschenkoi*). Other fish species (representing the suborder Teleostei, which have completely bony skeletons) whose sexual characteristics may be determined using the disclosed method include catfish (order Siluriformes), Florida pompano (*Trachinotus carolinus*), grouper (subfamily Epinephelinae), redfish (genus *Sebastes*), salmon (family Salmonidae), sea bass (various species), snapper (various species including those in the genus *Lutjanus*) and snook (various species including those in the family Centropomidae). The disclosed method may be used on live or dead fish including wild or domestically-raised fish, and may be used for a variety of purposes including research (for example, wild fish life history studies), conservation, stocking, consumption and aquaeulture. The disclosed method has particular value for determining the gender of immature live fish, for example aquaeulture-reared fish from whose female population roe will eventually be harvested.

The disclosed method and field test kit may be used to determine the readiness of individual fish for breeding. For example, female Florida pompano do not all become ready for breeding at the same age. The disclosed method enables selection of fish most likely to breed at a given time or selection of an appropriate time to breed individual fish.

The disclosed method and field test kit may be used to assess the maturity of eggs so as to enable roe harvesting at an appropriate maturity stage. If roe is harvested too early or too late, its taste characteristics may be less than optimal. In addition, undisturbed roe eventually is resorbed by the fish and this reduces obtainable yields.

The disclosed method and field test kit may be used to assess the influence of environmental or other factors affecting sexual development, sexual selection or hermaphroditism. This has particular value in fish research in both wild and aquaculture fish populations.

A variety of TGF-β superfamily peptide hormone concentrations may be measured using the disclosed method. Exemplary such peptide hormones include Anti-Müllerian hormone (AMH); bone morphogenetic proteins 2, 3, 4, 5, 6, 7, 8A, 8B, 10 or 15 (BMP2, BMP3, BMP4, BMP5, BMP6, BMP7, BMP8A, BMP9A, BMP10 or BMP15); growth differentiation factors 1, 2, 3, 3A, 5, 6, 7, 8, 9, 10 and 11 (GDF1, GDF2, GDF3, GDF3A, GDF5, GDF6, GDF7, GDF8, GDF9, GDF10 and GDF11); glial cell-derived neurotrophic factor (GDNF); Inhibin A (INHA); Inhibin B (INHB); Inhibin beta A, beta B, beta C or beta E (INHBA, INHBB, INHBC or INHBE); left right determination factors 1 or 2 (LEFTY1 or LEFTY2); Nodal; transforming growth factors beta 1, beta 2 or beta 3 (TGF-β1, TGF-β2 or TGF-β3); and combinations of any two or more such peptide hormones. Measuring the concentrations of two or more peptide hormones may provide improved accuracy in young fish and particularly in very young fish. Measurements of the concentration of one, any two or all of AMH, Inhibin A and Inhibin B are preferred, as are measurements of or involving Inhibin A concentration. Measurements may for example be performed using a variety of commercially or experimentally available techniques, with enzyme immunoassay (EIA) tests being preferred and enzyme-linked immunosorbent assay (ELISA) tests being especially preferred. EIA and ELISA test kits for testing humans or other mammals are commercially available from a number of suppliers including Beckman Coulter (for example the ACCESS™ Inhibin A Reagent Pack, cat. no. A36097), Cell Signaling Technology, Diagnostic Systems Laboratories (for example the Inhibin A ELISA kit, cat. no. DSL-10-28100-1), Enzo Life Sciences, Millipore Corp., Raybiotech, Inc., R&D Systems, Serotec Ltd. (for example the Ultra Sensitive Inhibin A Dimer Assay Kit, cat. no. MCA950KZZ), Sigma-Aidrich Co. and USCN Life Science Inc. The protocols and procedures specified by the manufacturer for human testing may in many cases be used without significant modification for testing fish, including the use of appropriate standards and controls. For example, approximately 1-2 ml of whole blood may be collected from the caudal vein of a fish and analyzed using ELISA. For live fish the blood sample desirably is obtained using a minimally invasive, non-lethal sampling method. Preferably sufficient serum or plasma is separated from the whole blood sample (for example using centrifuging or filtration) to provide about 0.5 ml serum or plasma from each fish. The serum, plasma or whole blood may if desired be stored (for example in a refrigerator) or frozen (for example in a freezer) prior to analysis, and warmed or thawed if need be when the analysis is later performed. Meanwhile, live fish may be marked using any suitable technique, stored (for example in a tank, pond or other suitable aqueous holding facility), and later (for example, one or more days later) retrieved for further processing after the desired concentration readings have been obtained. The collected blood, serum or plasma samples may be placed in the wells of microtiter plates coated with appropriate antibodies (for example, antibodies directed towards AMH, Inhibin A, Inhibin B or other members of the TGF-β superfamily). After incubation and washing steps, a detection antibody (for example, an antibody labeled with horseradish peroxidase) may be added to the wells followed by a substrate (for example, tetramethylbenzidine). Colorimetric changes may be measured at appropriate wavelengths using a microplate reader, with the measured absorbance being directly proportional to the peptide hormone concentration in the sample. Standard curves may be generated and used to determine the peptide hormone concentration in each sample. The results may be used to classify the fish, with the manner of classification generally depending upon the chosen peptide hormone and desired fish sexual characteristic. For example, in fish gender determination based on Inhibin A or Inhibin B, male sturgeon exhibit high measured peptide hormone concentrations (for example, concentrations above about 10, above about 15, above about 100, above about 200 or above about 300 picograms per milliliter or pg/ml depending in part on the age of the fish) and female sturgeon exhibit low measured peptide hormone concentrations (for example, concentrations below about 300, below about 200, below about 100, below about 15 or below about 10 pg/ml, again depending in part on the age of the fish). For fish gender determination in Florida pompano based on Inhibin B, male fish tend to exhibit low measured peptide hormone concentrations (for example, concentrations below about 50 pg/ml) and female fish tend to exhibit high measured peptide hormone concentrations (for example, concentrations above about 50 pg/ml). Fish gender determination based on AMH appears to be less discriminating than fish gender determination based on Inhibin A or Inhibin B, but female fish tend to exhibit lower measured peptide hormone concentrations than male fish. For roe maturity measurements based on Inhibin B, the peptide hormone concentration tends to be higher in fish with optimal roe and lower in fish without roe or with resorbed or overripe roe. An optimal time for roe harvest may accordingly correspond to fish having about 20 pg/ml or more observed Inhibin B concentration.

Preferably the test kit provides a rapid (for example, immediate or nearly immediate) peptide hormone concentration reading so that the desired fish sexual characteristic will be known shortly after a blood sample is taken, and without requiring time-consuming or expensive intermediate steps such as one or more of serum or plasma separation, freezing serum or plasma, shipping frozen serum or plasma to a remote laboratory, wet chemistry assay procedures, tagging fishes, return of the fish to a holding facility, retrieving fishes, or matching tags with laboratory assay data. For example, a field test kit employing a dip strip or other suitable indicating surface may be employed on or near water where fish reside. Desirably such a field test kit may be used to assess peptide hormone concentration readings in whole blood, serum or plasma samples right after blood samples have been drawn or otherwise obtained from fish. Current commercially available test kits typically require appreciable time to complete a concentration reading. If a test kit requires more than 15 minutes to complete a concentration reading then generally it will be necessary to mark, store and retrieve the fish as discussed above until after the concentration reading has been obtained. Desirably the test kit provides a suitably reliable reading (for example, 90% or greater accuracy when compared to histologically determined data) in a shorter time frame (for example in less than 15, 12, 10, 8, 5 or 4 minutes after exposure to a blood, serum or plasma sample, and preferably in less than 3, 2 or 1 minutes after exposure). This will enable a fish in water to be netted or otherwise made available for blood sampling, a blood sample to be extracted, a concentration reading to be obtained using the test kit and blood sample, and the fish (or fish having the desired sexual characteristic) to be promptly returned to water without asphyxiation once the desired sexual characteristic has been determined.

Because the consequences of a false positive or false negative determination will be less serious than would be the case in human testing, a field test kit may be selected or designed with an emphasis on speed, convenience of use and low per-test cost rather than an emphasis on accuracy or the avoidance of cross-contamination between samples, so that testing may more readily be performed within the time periods mentioned above. For example, a field test kit may be a hand-held device having a plurality (for example at least 3, 5, 10, 15 or 20) of test sites that can accept blood, serum or plasma samples and indicate peptide hormone concentrations. Individual test sites may be movable or detachable with respect to one other or with respect to the rest of the device. For example, each test site may be on a movable or detachable portion that can be removed or moved out of the way after accepting a sample so that additional fish may be tested on a fresh test site until the entire kit has been used up. The test site portions may be arranged in rows, for example as in a matchbook, so that the kit may be held in one hand and digits on the same hand may be used to move or detach used test sites. The test kit or test site portions may for example include an absorbent or nonabsorbent film, membrane or other support bearing a rapid-acting capture antibody (for example, for AMH, Inhibin A, Inhibin B or other members of the TGF-β superfamily) and a rapid-developing reporter antibody or other indicator that provides a colorimetric or other indication of peptide hormone concentration. To simplify use, the concentration indication may be expressed simply as a male or female prediction (for example, using a colorimetric gender symbol or alphabetic identifier). The test kit may be packaged in non-hermetic or non-sterile packaging to help reduce the per-test cost. For example, the test kit may include a paper or cardboard surround or other packaging that does not provide an appreciable barrier to moisture and which may be made without plastic films or metallic foils.

The invention is further illustrated in the following non-limiting examples, in which all parts and percentages are by weight unless otherwise indicated.

EXAMPLE 1

Figure 2:
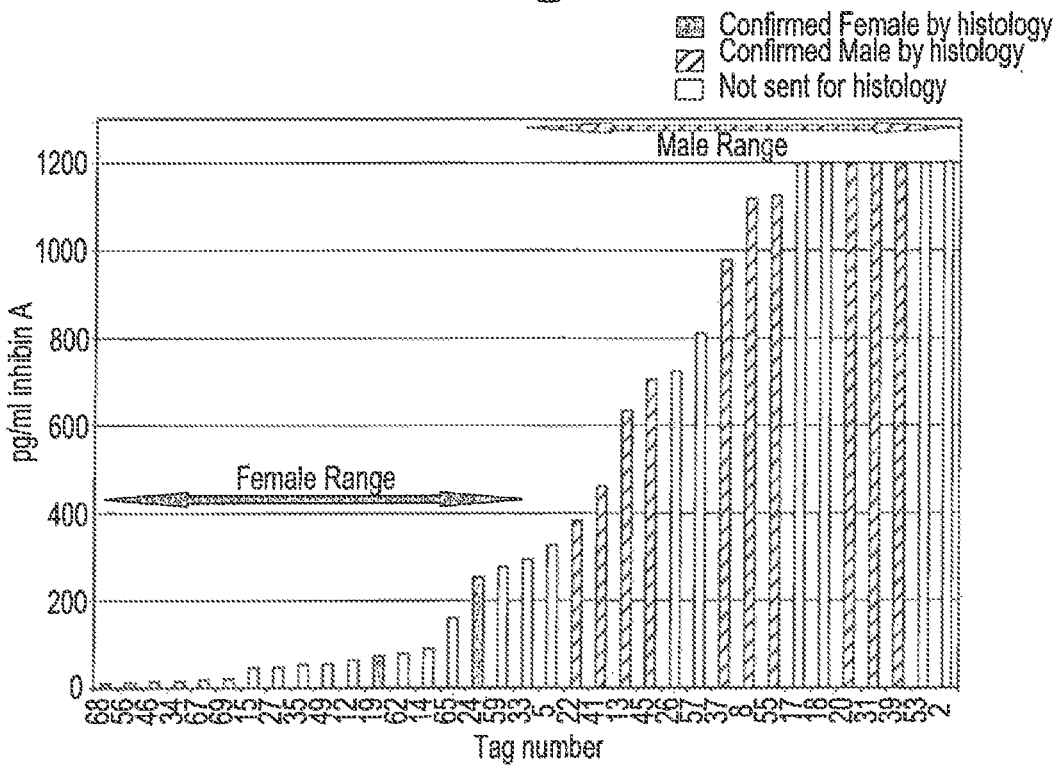
Figure 3:
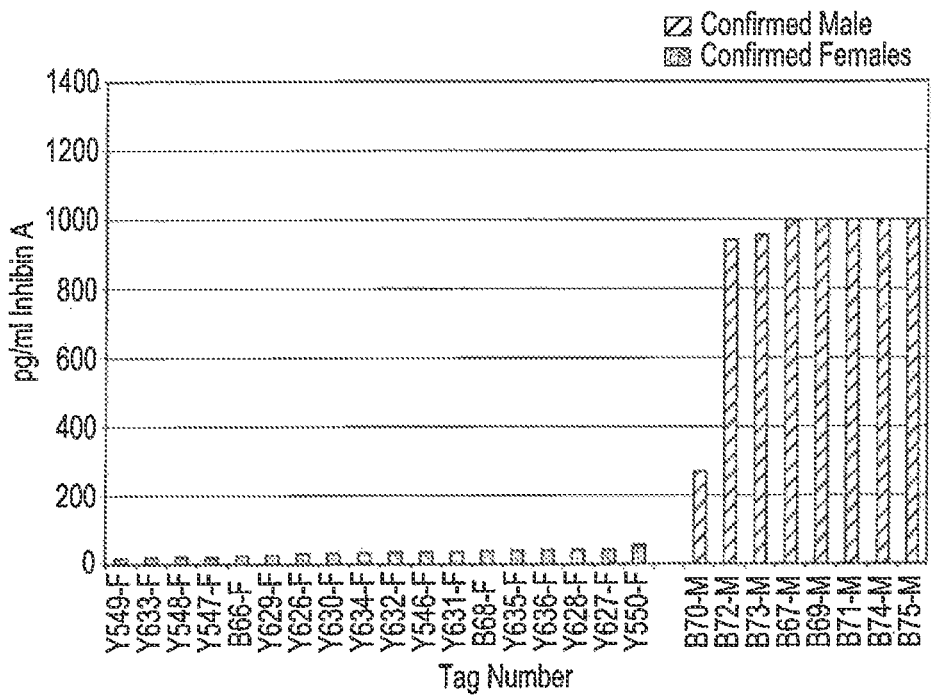

Whole blood samples were taken from collections of MAP-raised 16 month, 32 month and 39 month old Siberian sturgeon. The blood samples were centrifuged and serum from each sample was analyzed using ELISA test kits obtained from Beckman Coulter to determine Inhibin A concentrations. The fish were sacrificed and the sex of many or all of the fish in each collection determined histologically. For the 16 month old fish, histologic examination was used for 11 of 23 fish. For the 32 month old fish, histologic examination was used for 14 of 35 fish. All the 39 month old fish were histologically examined. The measured Inhibin A concentrations and a code identifying each fish and (where measured) its histologically-determined gender are respectively shown in FIG. 1, FIG. 2 and FIG. 3 for 16 month, 32 month and 39 month old fish. For the 16 month and 32 month old collections, half the fish were assumed to be of each gender and double-headed arrows depicting predicted female and male Inhibin A ranges were drawn on FIG. 1 and FIG. 2.

The results show that 16 month old female Siberian sturgeon had Inhibin A concentrations below about 13 pg/ml, and 16 month old male Siberian sturgeon had Inhibin A concentrations above about 13 pg/ml. Older fish had higher and somewhat more easily discriminated Inhibin A levels, with 32 month old female Siberian sturgeon having inhibin A concentrations below about 350 pg/ml and 32 month old male Siberian sturgeon having Inhibin A concentrations above about 350 pg/ml. 39 Month old Siberian sturgeon were even more easily identified, with females having Inhibin A concentrations below about 50 pg/ml and males having Inhibin A concentrations well above about 50 pg/ml. Ultrasound, a leading non-lethal method for fish sex determination, does not provide accurate results in young sturgeon, and especially in sturgeon less than three years old.

EXAMPLE 2

Figure 4:
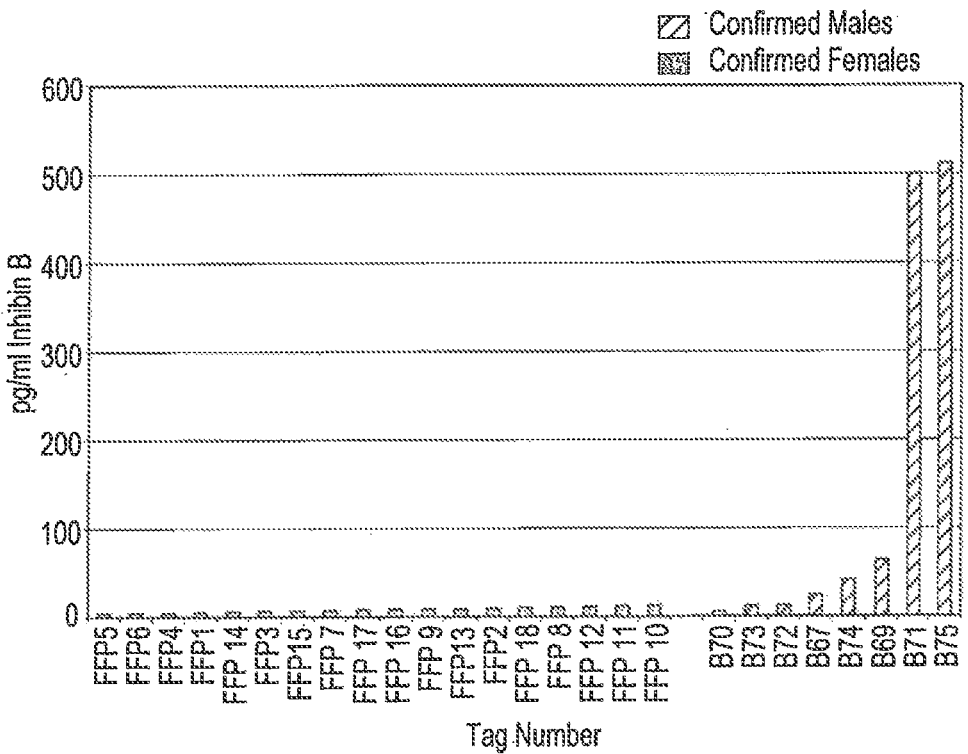
FIG. 4 and FIG. 5 are graphs illustrating Inhibin B concentrations in collections of 3 year and 5 year old Siberian sturgeon.
Figure 5:
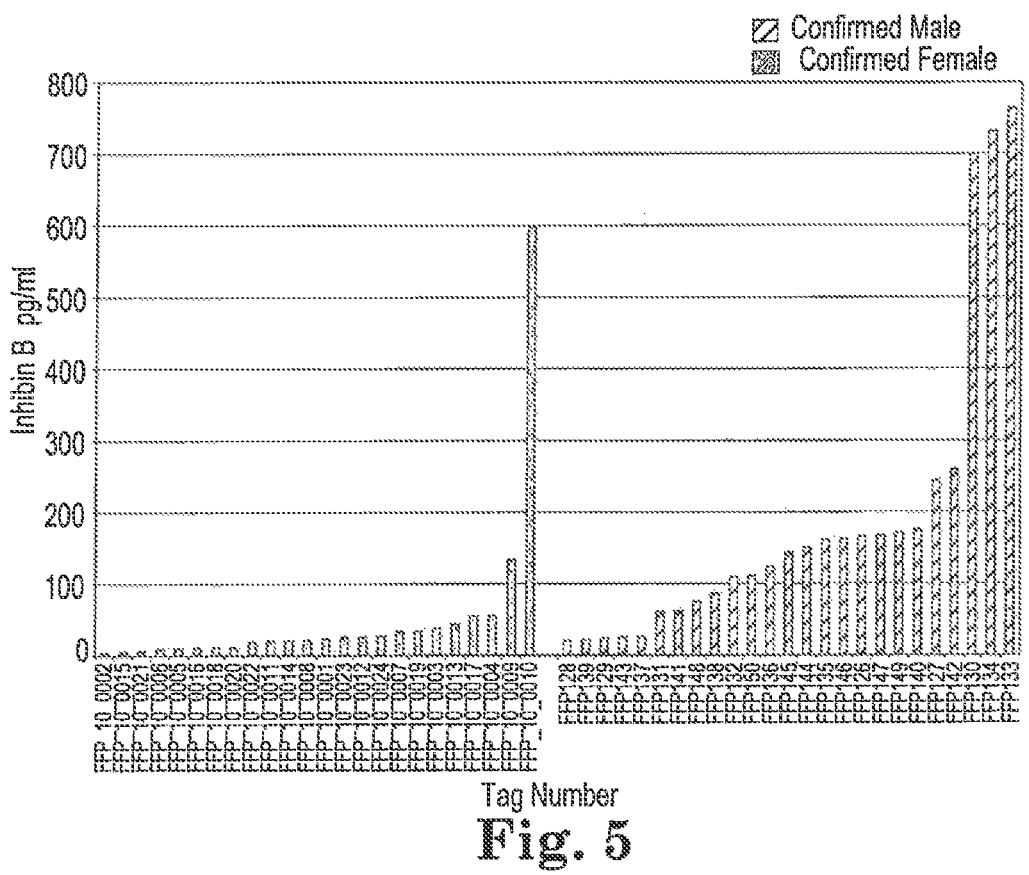

Using the method of Example 1, Inhibin B concentrations were measured in blood samples taken from 3 year and 5 year old Siberian sturgeon. The measured Inhibin B concentrations and a code identifying each fish and its histologically-determined gender are respectively shown in FIG. 4 and FIG. 5 for 3 year and 5 year old fish. The results in FIG. 4 show that most of the 3 year old female fish had Inhibin B concentrations below about 15 pg/ml, and most of the 3 year old male fish had Inhibin B concentrations above about 15 pg/ml. The results in FIG. 5 show that most of the 5 year old female fish had Inhibin B concentrations below about 50 pg/ml, and most of the 5 year old male fish had Inhibin B concentrations above about 50 pg/ml.

EXAMPLE 3

Figure 6:
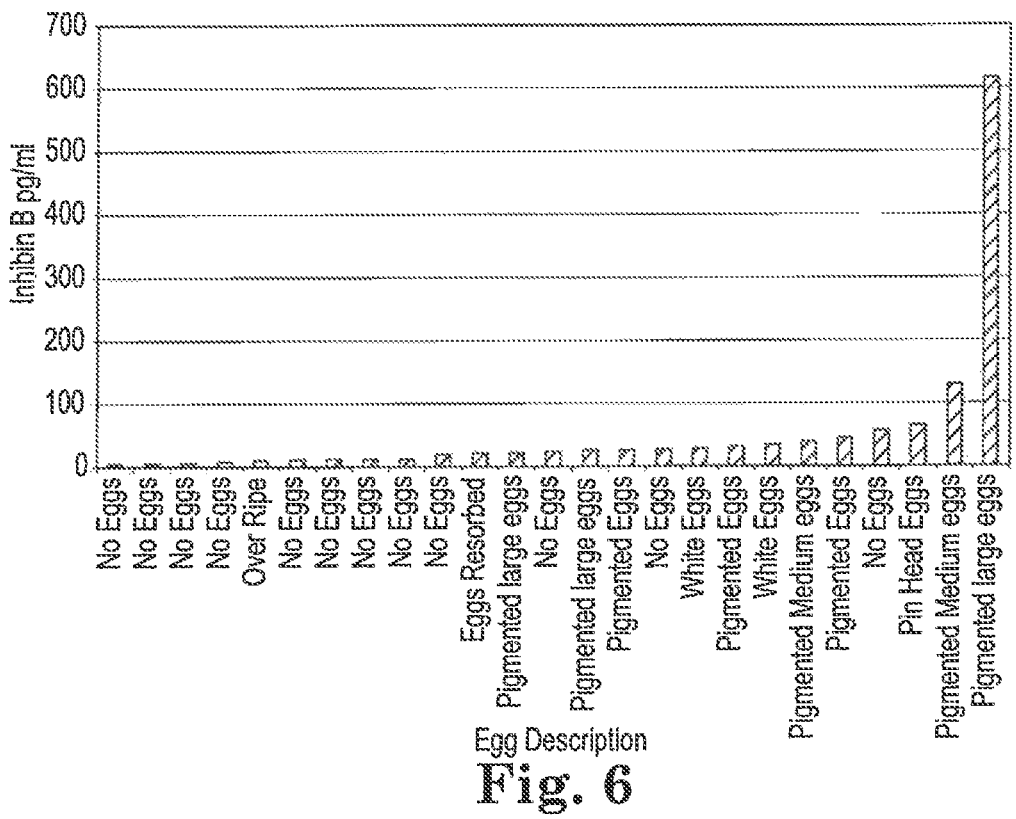
FIG. 6 is a graph illustrating Inhibin B concentrations and egg maturation in a collection of 5 year old Siberian sturgeon.

Using the method of Example 1, Inhibin B concentrations were measured in blood samples taken from 5 year old female Siberian sturgeon. The fish were also harvested to collect roe, and an assessment made of the roe characteristics (if present) and roe age. The measured Inhibin B concentrations and roe observations are shown in FIG. 6. The results show that female fish with desirable harvestable roe tended to have Inhibin B concentrations at or above about 20 pg/ml.

EXAMPLE 4

Two mature 5 year old sturgeons were examined using ultrasound and assessed to be males. Blood samples were then taken and analyzed for Inhibin A concentration using the method of Example 1. The resulting Inhibin A concentrations of 25.25 and 38.69 pg/ml correlated with ranges expected to correspond to female sturgeon. The fish were sacrificed and their gonads examined. This confirmed that both fish were actually female and that the results obtained using ultrasound were not correct.

EXAMPLE 5

Figure 7:
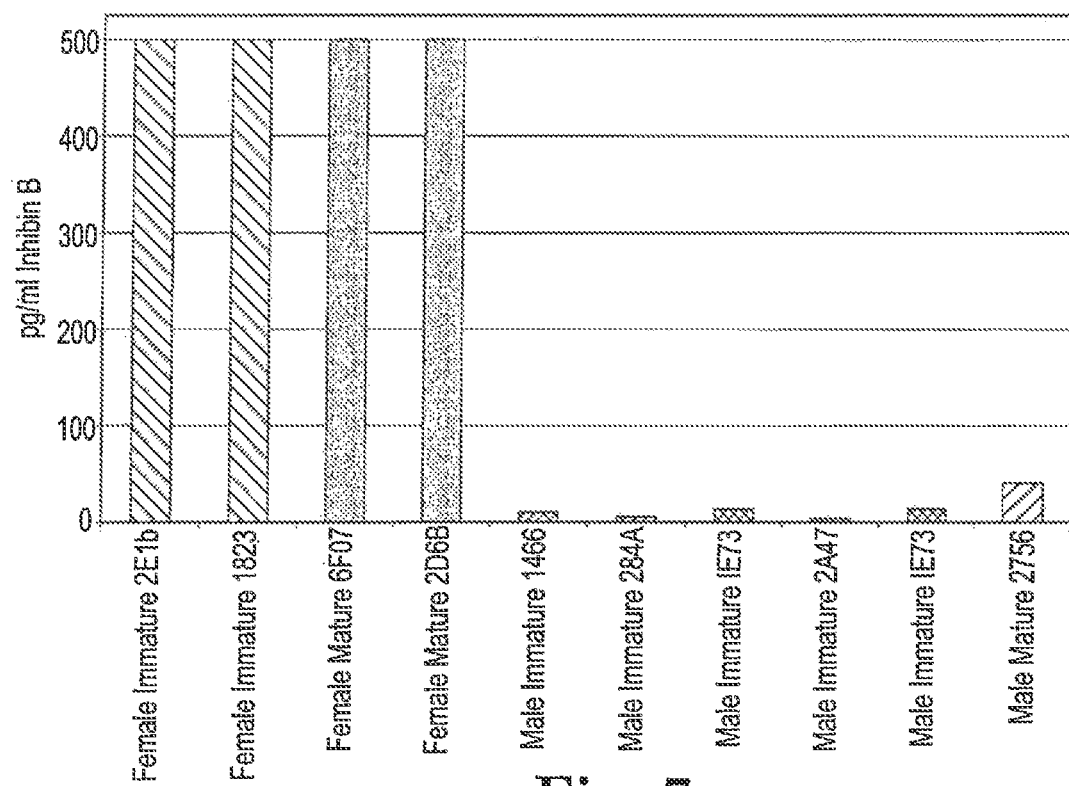
FIG. 7 is a graph illustrating Inhibin B concentrations in a collection of mature and immature Florida pompano.
Figure 8:
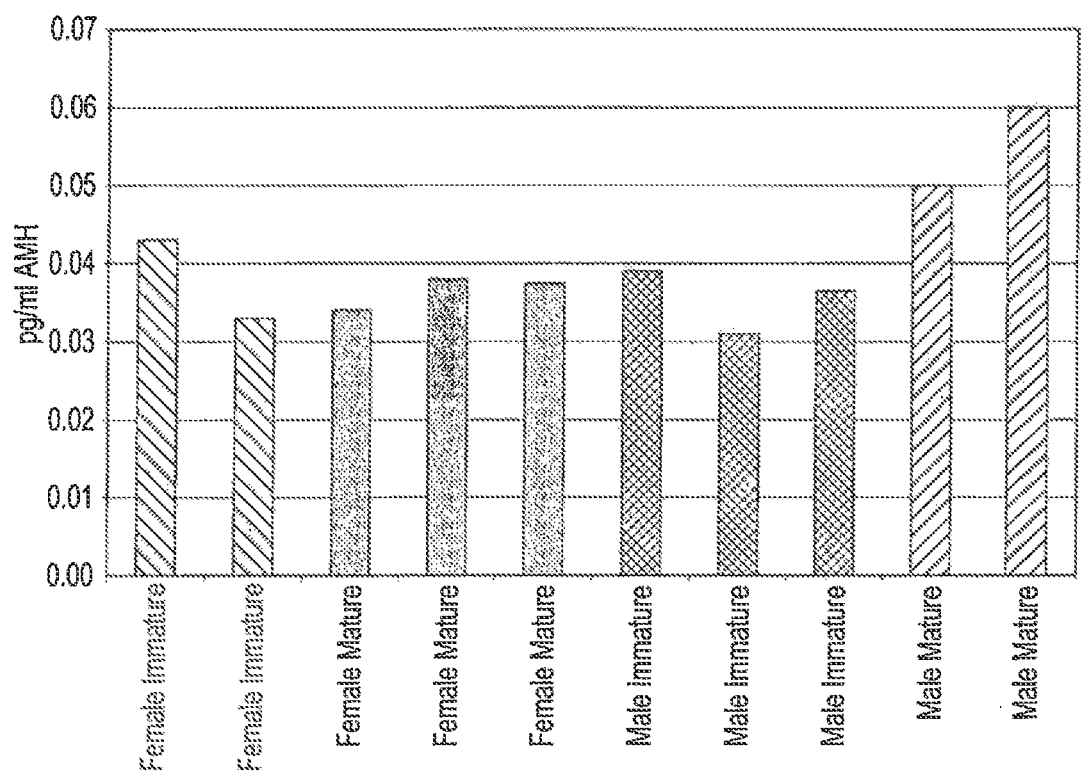
FIG. 8 is a graph illustrating AMH concentrations in a collection of mature and immature Florida pompano.

Using the method of Example 1, Inhibin B and AMH concentrations were measured in blood samples taken from mature and immature male and female Florida pompano. The results for Inhibin B and AMH are respectively shown in FIG. 7 and FIG. 8. Male fish had Inhibin B concentrations below about 50 pg/ml and female fish had Inhibin B concentrations above about 50 pg/ml. Female fish tended to exhibit lower measured AMH concentrations than male fish, with some overlap between individuals at the observed ages.

EXAMPLE 6

Using the method of Example 1, tanks containing 1 to 1.5 year old sturgeon could be analyzed to determine Inhibin A concentrations. Fish with Inhibin A concentrations below about 13 pg/ml could be culled and fish with Inhibin A concentrations above about 13 pg/ml could be raised to maturity and their roe harvested. The per-tank costs for performing the ELISA analysis would be significantly less than the cost of raising the culled fish for a further 3 to 4 years.

EXAMPLE 7

Figure 9:
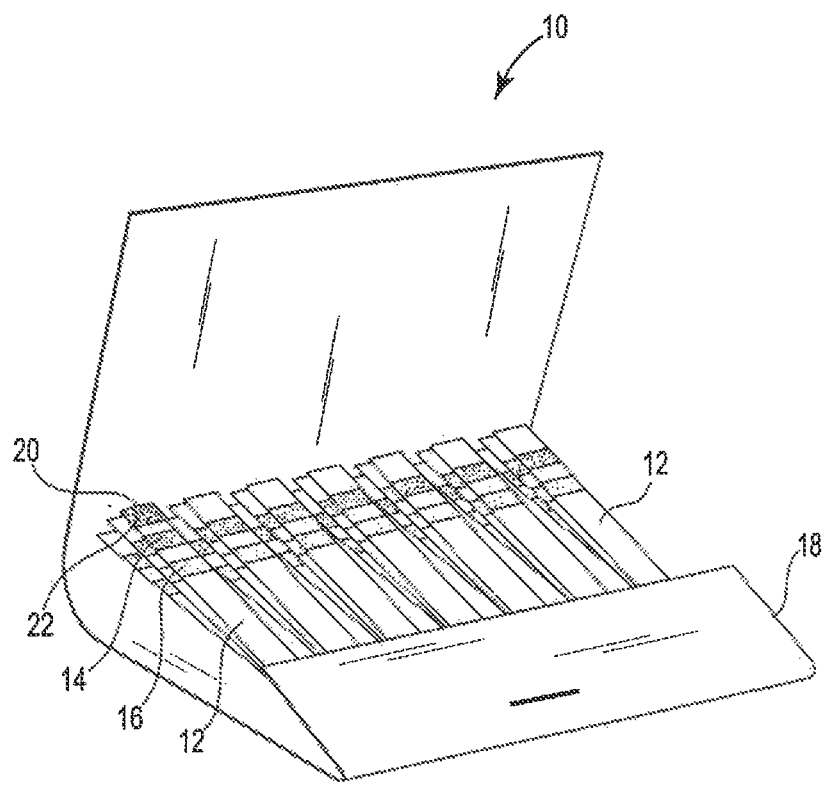
FIG. 9 is a field test kit determining fish sexual characteristics.

A handheld field test kit 10 like that shown in FIG. 9 may be made by coating portions of supports 12 with rapid-acting capture antibody 14 and rapid-developing reporter antibody 16 and encasing several rows of the supports in low-cost, protective but non-hermetic paper or cardboard packaging 18. The kit may be held in a single gloved or ungloved hand and desirably may be manipulated to expose fresh test sites using digits on the same hand. When a free end 20 of a support 12 is dipped in or otherwise exposed to a whole blood sample 22, blood travels past capture antibody 14 and reaches reporter indicator 16. The wicking or other fluid transmission characteristics of the supports 12 and the reactivity of capture antibody 14 and reporter indicator 16 are selected so that a colorimetric or other indication of peptide hormone concentration is provided in less than 15 minutes or such shorter time as may be selected to limit or prevent asphyxiation of fish while they are out of water. As each support is used, it may be moved (for example, folded) out of the way or detached (for example, torn away) so that additional supports will be exposed and tests may be performed for additional fish. Desirably, a series of fish are evaluated in production line fashion on or near the water, with samples being obtained and applied to test sites while peptide hormone concentration indications are still developing on prior test sites, and without having to mark or otherwise tag fish during the test.

Various modifications and alterations of this invention will be apparent to those skilled in the art without departing from this invention. This invention should not be restricted to that which has been set forth herein only for illustrative purposes.

The invention claimed is:

1. A field test kit for fish sexual characteristic determination, comprising a support bearing a blood, serum or plasma sample from a fish, a rapid-acting capture antibody and a rapid-developing reporter antibody or other indicator that provides a colorimetric or other indication of the concentration of one or more of the peptide hormones Inhibin A, Inhibin B, Inhibin beta A, Inhibin beta B, Inhibin beta C, Inhibin beta E and Anti-Müllerian hormone (AMH) in less than three minutes after exposure of the support to such fish blood, serum or plasma sample, and with 90% or greater accuracy when compared to histologically determined data.

2. A test kit according to claim 1, wherein the sample is whole blood.

3. A test kit according to claim 1, wherein the sample is serum.

4. A test kit according to claim 1, wherein the sample is plasma.

5. A test kit according to claim 1, wherein the sample is from an aquaculture-reared fish that is three years of age or less.

6. A test kit according to claim 1, wherein the sample is from an aquaculture-reared fish that is 1.5 years of age or less.

7. A test kit according to claim 1, wherein the sample is from a fish from the family Acipenseridae.

8. A test kit according to claim 1, wherein the sample is from a sturgeon.

9. A test kit according to claim 1, wherein the sample is from a fish of the subclass Teleostei.

10. A test kit according to claim 1, wherein the sample is from a salmon.

11. A test kit according to claim 1 wherein the peptide hormone comprises Anti-Müllerian hormone (AMH).

12. A test kit according to claim 1 wherein the peptide hormone comprises Inhibin A (INHA).

13. A test kit according to claim 1 wherein the peptide hormone comprises Inhibin B (INHB).

14. A test kit according to claim 1 wherein the peptide hormone comprises Inhibin beta A (INHBA).

15. A test kit according to claim 1 wherein the peptide hormone comprises Inhibin beta B (INHBB).

16. A test kit according to claim 1 wherein the peptide hormone comprises Inhibin beta C (INHBC).

17. A test kit according to claim 1 wherein the peptide hormone comprises Inhibin beta E (INHBE).

18. A test kit according to claim 1 wherein the peptide hormone comprises a combination of two or more of the peptide hormones Inhibin A, Inhibin B, Inhibin beta A, Inhibin beta B, Inhibin beta C, Inhibin beta E and AMH.

19. A test kit according to claim 1 in non-sterile packaging.

20. A test kit according to claim 1 wherein the indicator provides a colorimetric or other indication of peptide hormone concentration in less than three minutes.

\* \* \* \* \*